United States Patent [19]

Napp et al.

[11] 4,432,231
[45] Feb. 21, 1984

[54] ULTRASONIC LEVEL DETECTOR

[75] Inventors: E. Thomas Napp, Lake Zurich; R. C. Stauber, Hawthorn Woods; Thomas R. Lillegard, Crystal Lake, all of Ill.

[73] Assignee: Baxter Travenol Laboratories, Inc., Deerfield, Ill.

[21] Appl. No.: 392,984

[22] Filed: Jun. 28, 1982

[51] Int. Cl.³ .............................................. G01F 23/28
[52] U.S. Cl. .................................. 73/290 V; 73/644; 178/DIG. 13; 604/253
[58] Field of Search ................ 73/290 V, 644, 861.18, 73/702, 703, 431, 730; 310/334, 335, 336; 604/65, 66, 67, 253, 245; 128/DIG. 13

[56] References Cited

U.S. PATENT DOCUMENTS

| | | | |
|---|---|---|---|
| 4,187,720 | 2/1980 | Baker | 73/702 |
| 4,237,878 | 12/1980 | Kobayashi et al. | 128/DIG. 13 |
| 4,321,833 | 3/1982 | Zeiringer | 73/730 |
| 4,374,477 | 2/1983 | Kikuchi et al. | 73/861.18 |

Primary Examiner—Donald O. Woodiel
Attorney, Agent, or Firm—Paul C. Flattery; John A. Caruso

[57] ABSTRACT

An ultrasonic detector, particularly useful in the level detection of blood within an arterial reservoir, is provided. The detector includes a pair of opposed arms for connection to the arterial reservoir. One of the arms carries a transmitting transducer while the other arm carries a receiving transducer facing the transmitting transducer. A clamping ring is slidable on both arms for forcing the arms toward each other when the ring is moved in one direction and for enabling the arms to move apart from each other when the ring is moved in the opposite direction.

14 Claims, 7 Drawing Figures

ULTRASONIC LEVEL DETECTOR

TECHNICAL FIELD

The present invention concerns an ultrasonic level detector and, more particularly, a hand-installable ultrasonic level detector.

BACKGROUND ART

Ultrasonic detectors conventionally utilize a transmitting crystal and a receiving crystal, and are used for fluid level detection, bubble detection and the like. The ultrasonic detector housing must be securely connected to the container being sensed, i.e., the flow tube or reservoir, in order to provide accurate readings. Some prior art ultrasonic detector housings utilize a compressible material between the ultrasonic transducers and the housing to hold the housing in place. Because the compressible material allows very little movement of the transducers, close dimensional tolerances are required on the container where the housing attaches to it in order to apply sufficient contact pressure to the transducers. Certain prior art housings have separate mechanical springs that render them complicated to build and difficult to clean.

An important use of ultrasonic detectors is in oxygenation in hospitals, where the blood level in an arterial reservoir is sensed by an ultrasonic level detector. For such an application, it is important that the ultrasonic level detector housing have the ability to be set in place on the container rapidly and easily, and that the housing be easy to clean. A most desirable detector housing would be one that enables easy one-hand attachment and removal; one that cannot be overtightened, one that includes few parts for ease of assembly, and one that utilizes smooth, easy to clean surfaces.

DISCLOSURE OF THE INVENTION

In accordance with the present invention, an ultrasonic detector is provided that may be installed by hand, is easy to tighten onto the container to be sensed, utilizes few parts for ease of assembly and incorporates smooth easy to clean surfaces.

Applicants's ultrasonic detector comprises a pair of opposed arms for connection to the container which carries the fluid to be sensed. One of the arms carries a transmitting transducer and the other arm carries a receiving transducer which faces the transmitting transducer. A clamping ring is provided, which is slidable on both arms for forcing the arms toward each other when the ring is moved in one direction and for enabling the arms to move apart from each other when the ring is moved in an opposite direction.

In the illustrative embodiment, each arm comprises a front portion carrying one of the transducers and adapted for engagement with the container, a contiguous intermediate portion on which the clamping ring is slidable, and a contiguous rear portion that is fastened to the rear portion of the other arm. Each of the transducers is potted in a resilient material which deforms to substantially comply with the surface of the container.

In the illustrative embodiment, the front portion of each arm has a generally planar clamping surface except for the surface of the transducer carried thereon. The rear portions operate to provide a hinge for the front and intermediate portions of the arms. Each of the arms is formed of plastic and defines a slot for carrying therein an electrically conductive wire from the transducer.

A more detailed explanation of the invention is provided in the following description and claims, and is illustrated in the accompanying drawings.

DETAILED DESCRIPTION OF THE ILLUSTRATIVE EMBODIMENT

Figure 1:
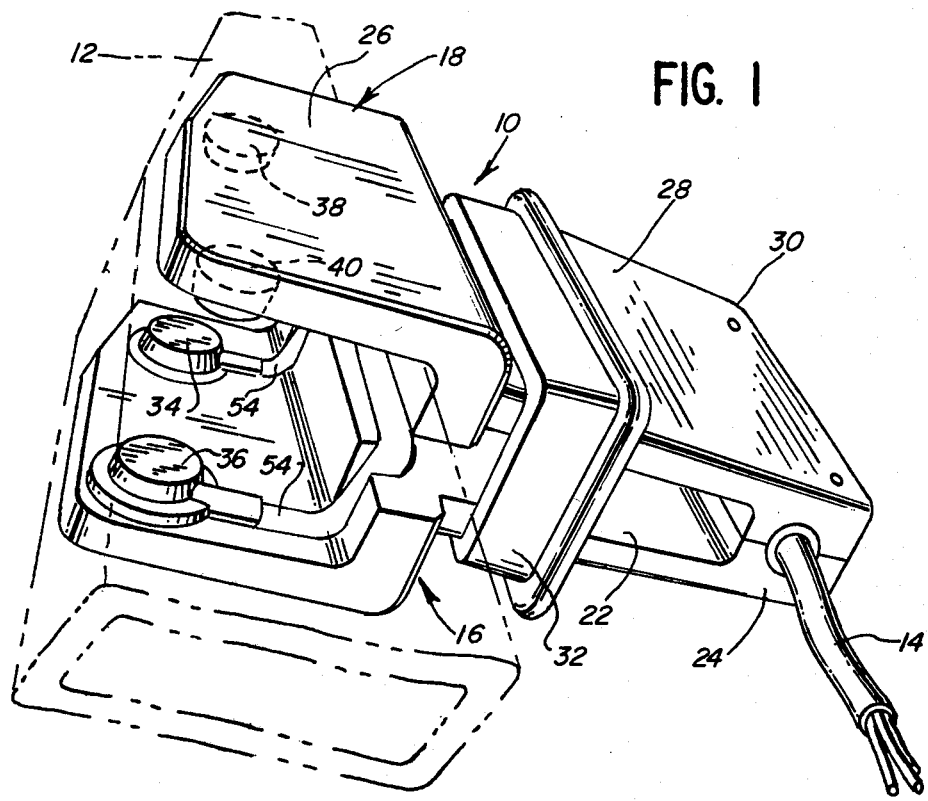
FIG. 1 is a perspective view of an ultrasonic detector constructed in accordance with the principles of the present invention.
Figure 2:
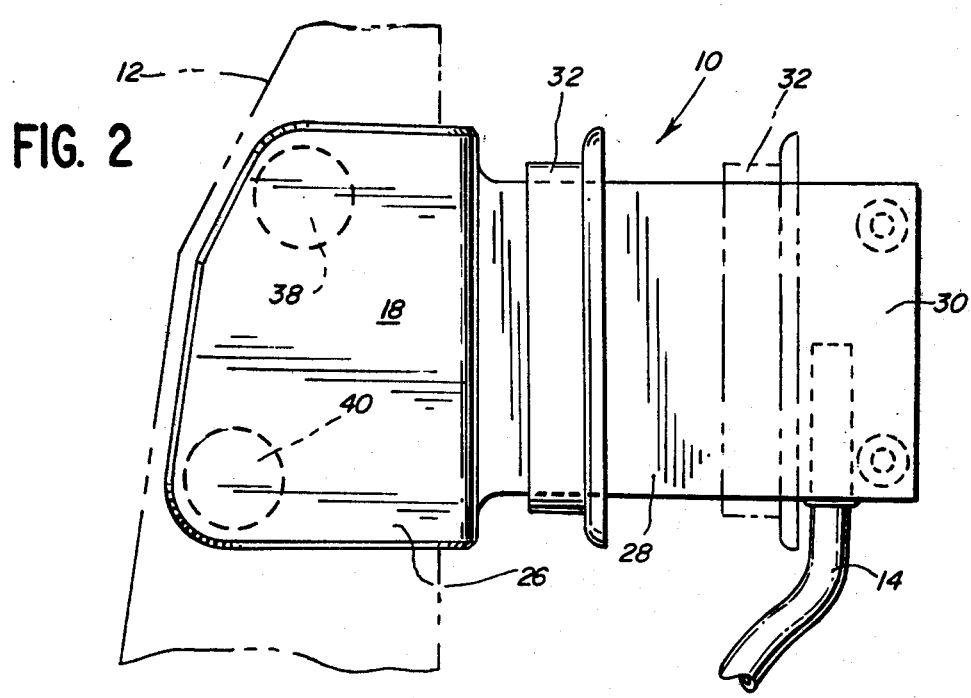
FIG. 2 is a side elevational view thereof, showing a portion of the container and the slidability of the clamping ring in dashed lines.

Referring to the drawings, the ultrasonic detector shown therein is particularly useful for blood level detection in an arterial reservoir of a blood oxygenator. Ultrasonic detector 10 clamps to the outside walls of arterial blood reservoir 12 of the oxygenator and is electrically connected via electrical line 14 to an alarm control box.

Ultrasonic detector 10 comprises a first arm 16 formed of a suitable plastic material and a second arm 18 also formed of a suitable plastic material. First and second arms 16, 18 are similar to each other in that they are the mirror image of each other. Arm 16 comprises a front portion 20, a contiguous intermediate portion 22 and a rear portion 24. Likewise, arm 18 comprises a front portion 26, a contiguous intermediate portion 28, and a contiguous rear portion 30. A clamping ring 32 is provided around intermediate portions 22 and 28, and is slidable on the intermediate portions.

Figure 5:
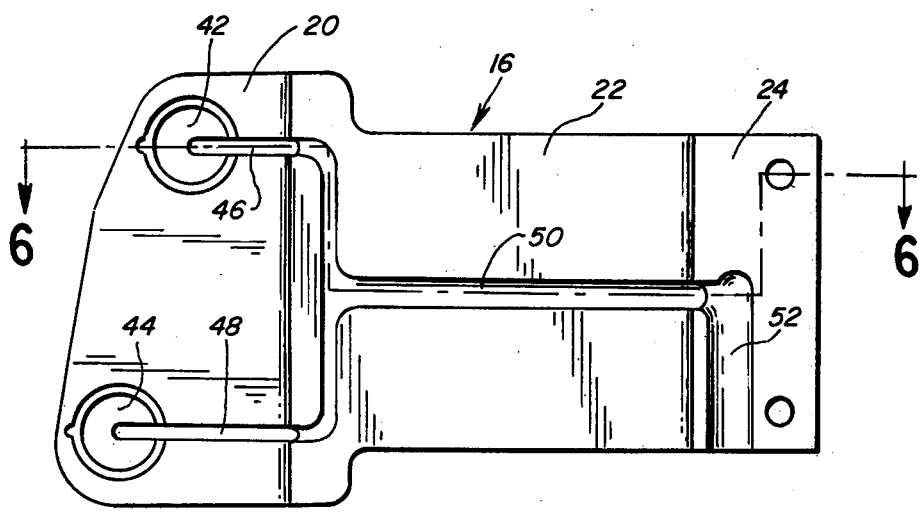
FIG. 5 is an elevational view of the inside structure of one of the arms with the transducers and electrical wiring removed.
Figure 6:
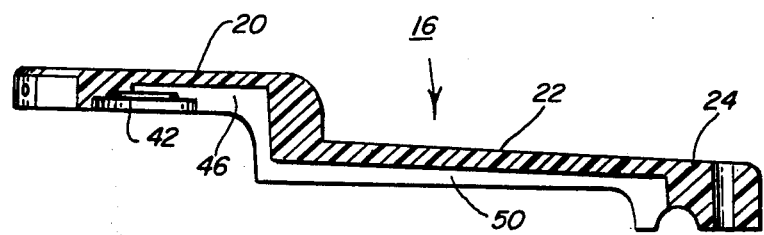
FIG. 6 is a cross-sectional view thereof, taken along the plane of the line 6—6 of FIG. 5.
Figure 7:
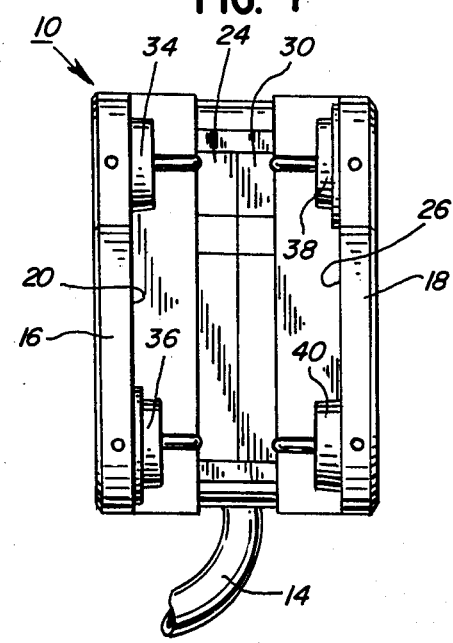
FIG. 7 is a front view of the ultrasonic level detector of FIGS. 1-4.

Arm 16 carries an upper transmitting transducer 34 and a spaced, lower transmitting transducer 36, both on front portion 20. Front portion 26 of arm 18 carries an upper receiving transducer 38, which faces transmitting transducer 34, and a lower receiving transducer 40 which faces lower transmitting transducer 36. Transducers 34, 36, 38 and 40 comprise crystal transducers which are potted in a resilient material which deforms to substantially comply with the surface of reservoir 12. It is preferred that the resilient potting compound be RTV. As illustrated most particularly in FIGS. 5 and 6, each arm defines a pair of recesses 42, 44 for receiving the upper transducer within recess 42 and the lower transducer within recess 44. In addition, each arm defines contiguous slots 46, 48, 50 and 52 for receiving and carrying therein electrically conductive wire 54 (FIG. 1) from the transducers.

As illustrated in the drawings, each arm has a clean, smooth outside surface and the inside surface of the front portions are planar except for the transducers. Intermediate portions 22, 28 and rear portions 24, 30 are constructed so that when rear portions 24 and 30 are coupled together and fastened by suitable fastening means 56 (FIGS. 3 and 4) a hinge is effectively provided.

Figure 3:
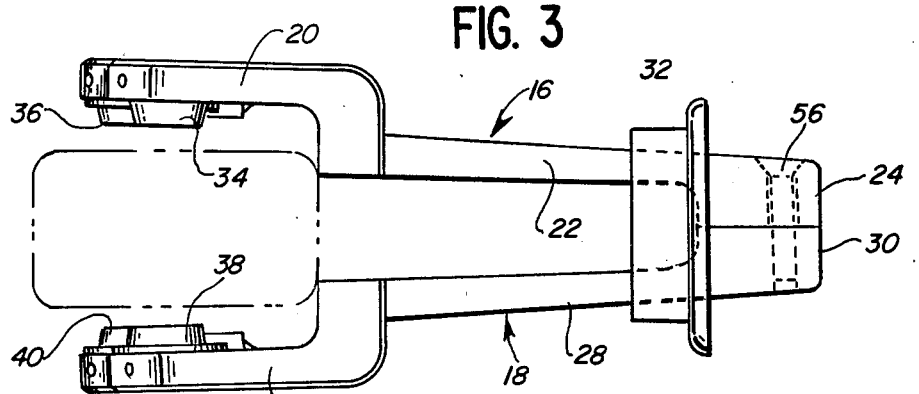
FIG. 3 is a top plan view thereof, showing the arms in their front clamp condition.
Figure 4:
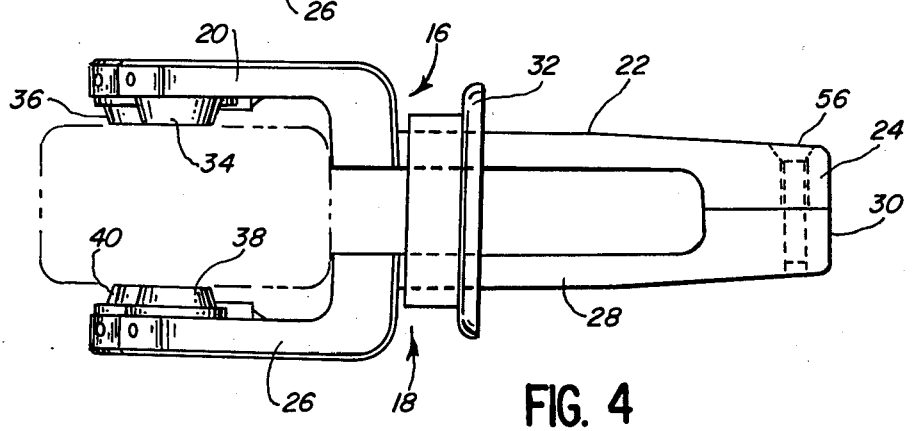
FIG. 4 is a top plan view thereof, similar to FIG. 3 but showing the arms in their clamped position.

As illustrated in FIG. 3, when clamping ring 32 is in its rearward position, arms 16 and 18 move apart from each other as a result of the resiliency of the arms so that the arterial container can be placed between the clamping front portions 20 and 26. Once the arterial container is in place, clamping ring 32 is slid in the forward direction as illustrated in FIG. 4, to clamp the front portions 20 and 26 onto the surface of the arterial reservoir. The natural resilience of the plastic housing material provides the spring force necessary to bring the transducers into secure engagement with the reservoir walls.

The electrical wiring 14 couples the transducers to an alarm control box. Lower transducers 36 and 40 will operate to warn of blood levels if the blood level is below these transducers, to thereby trigger an alarm. Upper transducers 34 and 38 will operate to shut off the blood flow when the blood level has reached these transducers.

It is understood, however, that the ultrasonic detector described herein may be utilized for level and/or bubble detection of various fluids.

Although an illustrative embodiment of the invention has been shown and described, it is to be understood that various modifications and substitutions may be made by those skilled in the art without departing from the novel spirit and scope of the present invention.

What is claimed is:

1. An ultrasonic detector, which comprises:
   a pair of opposed arms for connection to a container which carries fluid to be sensed;
   one of the arms carrying a transmitting transducer and the other arm carrying a receiving transducer which faces the transmitting transducer; and
   a clamping ring that is slidable on both arms for forcing the arms toward each other when the ring is moved in one direction and for enabling the arms to move apart from each other when the ring is moved in a direction opposite to the one direction.

2. An ultrasonic detector as described in Claim 1, in which each arm comprises a first portion carrying one of the transducers and adapted for engagement with the container, a contiguous intermediate portion on which the clamping ring is slidable, and a contiguous rear portion that is fastened to the rear portion of the other arm.

3. An ultrasonic detector as described in claim 2, in which each said front portion has a generally planar clamping surface except for the surface of the transducer carried thereon.

4. An ultrasonic detector as described in claim 2, said rear portions operating to provide a hinge for the front and intermediate portions.

5. An ultrasonic detector as described in claim 1, in which each of the transducers is potted in a resilient material which deforms to substantially comply with the surface of the container.

6. An ultrasonic detector as described in claim 5, said resilient material comprising RTV.

7. An ultrasonic detector as described in claim 6, in which each arm defines a recess for receiving the RTV-potted transducer.

8. An ultrasonic detector as described in claim 1, in which the container comprises a reservoir having generally planar surfaces to which the detector is connected.

9. An ultrasonic detector as described in claim 1, in which the container comprises a flow tube having generally planar surfaces to which the detector is connected.

10. An ultrasonic detector as described in claim 1, each of said arms being formed of plastic and defining a slot for carrying therein an electrically conductive wire from the transducer.

11. An ultrasonic detector as described in claim 10, each of said arms being formed of plastic and defining slots for carrying therein electrically conductive wires from the transducers.

12. An ultrasonic detector as described in claim 1, each of said arms carrying an upper level transducer and a lower level transducer.

13. An ultrasonic detector, which comprises:
   a pair of opposed arms for connection to a container which carries fluid to be sensed;
   one of the arms carrying a transmitting transducer and the other arm carrying a receiving transducer which faces the transmitting transducer;
   a clamping ring that is slidable on both arms for forcing the arms toward each other when the ring is moved in one direction and for enabling the arms to move apart from each other when the ring is moved in a direction opposite to the one direction;
   each arm comprising a front portion carrying one of the transducers and adapted for engagement with the container, a contiguous intermediate portion on which the clamping ring is slidable, and a contiguous rear portion that is fastened to the rear portion of the other arm;
   each of the transducers being potted in a resilient material which deforms to substantially comply with the surface of the container; and
   said rear portions operating to provide a hinge for the front and intermediate portions.

14. An ultrasonic detector as described in claim 13, wherein each of said arms carries an upper level transducer and a lower level transducer; and each of said arms is formed of plastic and defines slots for carrying therein electrically conductive wires from the transducers.

* * * * *